US00PP33094P2

(12) United States Plant Patent
Verschoor

(10) Patent No.: US PP33,094 P2
(45) Date of Patent: May 25, 2021

(54) ***VERONICA* PLANT NAMED 'VERPURG'**

(50) Latin Name: *Veronica spicata*
Varietal Denomination: Verpurg

(71) Applicant: Janus Verschoor, Haarlem (NL)

(72) Inventor: Janus Verschoor, Haarlem (NL)

(73) Assignee: A. VERSCHOOR HORTICULTURE, Haarlem (NL)

( * ) Notice: Subject to any disclaimer, the term of this patent is extended or adjusted under 35 U.S.C. 154(b) by 0 days.

(21) Appl. No.: 16/945,276

(22) Filed: Jul. 31, 2020

(51) Int. Cl.
*A01H 6/68* (2018.01)
*A01H 5/02* (2018.01)

(52) U.S. Cl.
USPC ..... Plt./251

(58) Field of Classification Search
USPC ..... Plt./251
See application file for complete search history.

*Primary Examiner* — Annette H Para
(74) *Attorney, Agent, or Firm* — Penny J. Aguirre

(57) ABSTRACT

A new cultivar of *Veronica* plant named 'Verpurg' that is characterized by its compact and dwarf plant habit, its numerous flowering stems, its re-blooming habit resulting in a long bloom season, its flowers that are intense violet-purple in color, and its strong flower stems.

2 Drawing Sheets

Botanical classification: *Veronica spicata.*
Cultivar designation: 'Verpurg'.

CROSS REFERENCE TO A RELATED APPLICATION

This application is related to U.S. Plant Patent for a plant derived from the same breeding program that is entitled *Veronica* Plant Named 'Verspi' (U.S. Plant Pat. No. 29,780).

BACKGROUND OF THE INVENTION

The present invention relates to a new and distinct cultivar of *Veronica spicata* and will be referred to hereafter by its cultivar name, 'Verpurg'. 'Verpurg' represents a new herbaceous perennial grown for landscape use.

'Verpurg' arose from open pollination of *Veronica* 'Verspi' as the female parent. 'Verpurg' originated as a seedling that arose from seed planted from open pollination of *Veronica* 'Verspi' in 2016. The male parent is therefore unknown. 'Verpurg' was selected as a single unique plant in 2018 from amongst the resulting seedlings.

Asexual propagation of the new cultivar was first accomplished by stem cuttings by the Inventor in July of 2019 in Haarlem, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Verpurg' as a unique cultivar of *Veronica.*

1. 'Verpurg' exhibits a compact and dwarf plant habit.
2. 'Verpurg' exhibits numerous flowering stems.
3. 'Verpurg' exhibits a re-blooming habit resulting in a long bloom season.

4. 'Verpurg' exhibits flowers that are intense violet-purple in color.
5. 'Verpurg' exhibits strong flower stems.

The female parent of 'Verpurg', 'Verspi', is similar to 'Verpurg' in in having compact, dwarf plant habit and a floriferous blooming habit. 'Verspi' differs from 'Verpurg' in having flowers that are pink in color. 'Verpurg' can be compared to the *Veronica spicata* cultivar 'Purpleicious' (U.S. Plant Pat. No. 17,639). 'Verspi' is similar to 'Verpurg' in having compact, dwarf plant habit and a floriferous blooming habit. 'Verspi' differs from 'Verpurg' in having flowers that are pink in color. 'Purpleicious' is similar to 'Verpurg' in having flowers that are purple in color. 'Purpleicious' differs from 'Verpurg' in having a shorter bloom period (commences bloom later in season), in being taller in height (less compact), and in having shorter flower stems.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to a website listing by Concept Plants, the breeder's representative for licensing (Concept Plants does not sell plants) and Kientzler (a licensee of Concept Plants that produces unrooted cuttings for growers).

BRIEF DESCRIPTION OF THE DRAWINGS

The accompanying colored photographs illustrate the overall appearance and distinct characteristics of the new *Veronica*. The photographs were taken of a one-year-old plant of 'Verpurg' as field grown in Haarlem, The Netherlands and placed in a container for the photograph.

The photograph in FIG. 1 provides a side view of a plant of 'Verpurg' in bloom.

Figure 1:
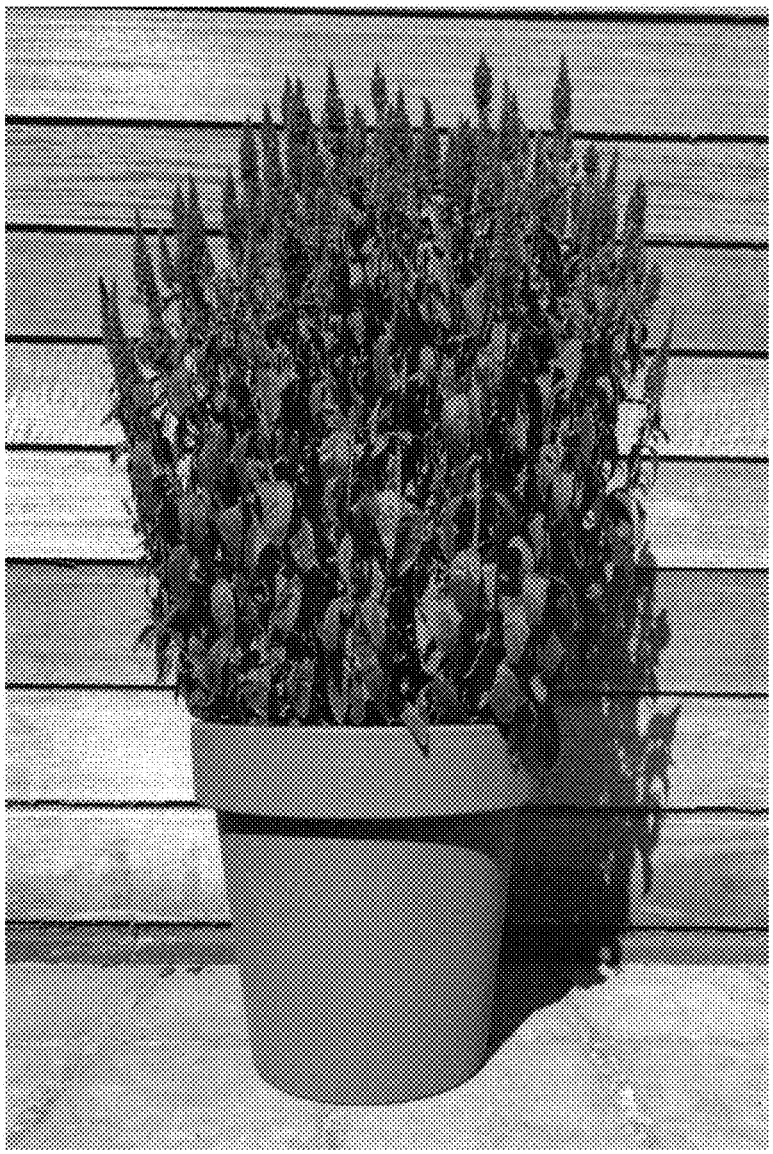
Figure 2:
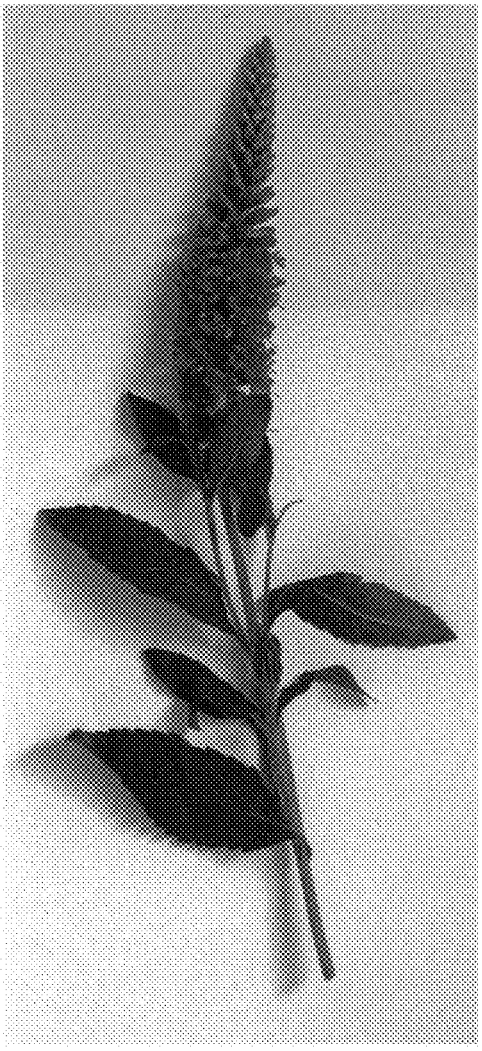

The photograph in FIG. 2 provides a close-up view of an inflorescence and leaves of 'Verpurg'.

The colors in the photographs may differ slightly from the color values cited in the detailed botanical description, which accurately describe the colors of the new *Veronica*.

DETAILED BOTANICAL DESCRIPTION

The following is a detailed description of the new cultivar as observed for a plant one year in age as field grown outdoors in Haarlem, The Netherlands. The phenotype of the new cultivar may vary with variations in environmental, climatic, and cultural conditions, as it has not been tested under all possible environmental conditions. The color determination is in accordance with The 2005 Colour Chart of The Royal Horticultural Society, London, England, except where general color terms of ordinary dictionary significance are used.

General description:

*Blooming period*.—Late spring into summer and re-blooming in autumn in The Netherlands.

*Plant type*.—Herbaceous perennial.

*Plant habit*.—Compact, dwarf.

*Height and spread*.—Reaches about 54 cm in height and 48 cm in spread as a one-year-old field-grown plant.

*Hardiness*.—At least in U.S.D.A. Zones 4 to 9.

*Diseases and pests*.—Good resistance to powdery mildew (typically caused by *Sphaerotheca* sp.) has been observed, no susceptibility or resistance to pests has been observed.

*Propagation*.—Stem cuttings.

*Root development*.—About 1.5 weeks to initiate roots and 3 to 4 weeks to produce a young plant from a rooted cutting.

*Growth rate and vigor*.—Low to moderate.

Stem description:

*Shape*.—Round.

*Stem quantity*.—Average of 36 main branches, 6 secondary branches per branch.

*Stem color*.—Young stems; 144A, mature stems and internodes; 143C.

*Stem size*.—Average of 4 mm in diameter and 36 (excluding inflorescence) in length.

*Stem surface*.—Slightly glossy and densely covered with soft pubescence hairs; an average of 0.2 mm in length and too fine to measure color.

*Stem strength*.—Strong.

*Stem aspect*.—Held at an average angle of 20° to vertical.

*Branching habit*.—Freely branching from the base.

*Internode length*.—Average of 3.5 cm.

Foliage description:

*Leaf division*.—Simple.

*Leaf arrangement*.—Opposite.

*Leaf shape*.—Narrow ovate.

*Leaf size*.—An average of 6.4 cm in length and 2.2 cm in length.

*Leaf number*.—Average of 18 per branch.

*Leaf base*.—Attenuate.

*Leaf apex*.—Acute.

*Leaf margin*.—Crenate-serrate.

*Leaf venation*.—Pinnate, upper surface 144A in color, lower surface 143B in color.

*Leaf surface*.—Upper surface slightly glossy, lower surface matte, both surfaces slightly covered with very short pubescent hairs; too fine to measure color, average length of hairs is 0.2 mm in length.

*Leaf color*.—Young upper and lower surface; 137B, mature upper surface; 137A, mature lower surface; 137C.

*Petiole*.—Average of 1.8 cm in length, 3 mm in diameter, both surfaces slightly glossy and slightly pubescent covered with very short hairs; an average of 0.2 mm in length and too small to measure color, strong, upper surface color 137C, changing to 143C at the base, lower surface color 137C.

Flower description:

*Inflorescence type*.—Compound terminal racemes of rotate-shaped flowers.

*Lastingness of inflorescence*.—Individual flowers last an average of 7 days, self-cleaning, inflorescence lasts about 3 weeks.

*Inflorescence size*.—Average of 7.8 cm in height and 2 cm in diameter.

*Inflorescence density*.—Very dense.

*Flower type*.—Terminal and axillary racemes.

*Flower number*.—Average of 200 per inflorescence, 5,000 per plant.

*Flower aspect*.—Outward facing.

*Flower fragrance*.—None.

*Flower buds*.—Ovate in shape, smooth and glabrous, matte surface, average of 5 mm in length and 2 mm in diameter, 77B to N81B in color, immature calyx 137C in color.

*Flower size*.—About 7 mm in depth and width.

*Flower shape*.—Campanulate.

*Peduncle*.—7.8 cm in length and 2 mm in diameter, held vertically, strong, 143B in color, surface is matte and covered with soft, short pubescence; an average of 2 mm in length and too small to measure color.

*Pedicels*.—An average of 0.5 mm in length and width, held at an average angle of 45°, moderately strong, 138B in color, surface is matte and covered with soft, short pubescence; an average of 2 mm in length and too small to measure color.

*Calyx*.—Rotate in shape, average of 4 mm in length and 2.5 mm in diameter.

*Sepals*.—4, rotate, 1 whorl, ovate in shape, base is broad cuneate, acute apex, entire margins, acute apex, lower sepals 4 mm in length and 1 mm in width, upper sepals 3 mm in length and 1 mm in width, color; upper surface when opening and fully open 137C, lower surface when opening and fully open 138B, upper surface matte, upper and lower surface covered with soft, short pubescence; 0.2 mm in length and too small to measure color.

*Petals*.—4, 1 whorl, ovate to obovate in shape, acute apex, lower 35% fused, lobes; entire margin, both surfaces glabrous and matte, average of 7 mm in length and 3.5 mm in width, color when opening upper and lower surface N81B, color when fully open and fully open upper and lower surface N81B to 77A, throat; 2 mm in length, both surfaces glabrous, N87A in color, tube; 2.5 mm in length, 1.5 mm in width, outer surface is glabrous, inner surface densely covered with soft hairs; 0.75 mm in length and NN155D in color, color of tube inner and outer surface N81B and 77A.

Reproductive organs:

*Gynoecium*.—Pistil; 1, 6 mm in length, style; 5 mm in length, 70D in color, stigma; club-shaped, 77A in color, ovary; 144C in color.

*Androecium*.—Stamens; 2, filament; 5 mm in length, 77A in color, anthers; double kidney shaped, 1 mm in length, 0.75 mm in width, a color between N186A and N186C in color, pollen; moderate in quantity, 4C in color.

*Fruit*.—Fruit and seed production has not been observed to date.

It is claimed:

1. A new and distinct cultivar of *Veronica* plant named 'Verpurg' as herein illustrated and described.

* * * * *